United States Patent [19]

Reinhold et al.

[11] Patent Number: 4,716,246
[45] Date of Patent: Dec. 29, 1987

[54] PROCESS FOR L-DOPA

[75] Inventors: Donald F. Reinhold, Morganville; Torleif Utne, Warren; Newton L. Abramson, Edison, all of N.J.

[73] Assignee: Merck & Co., Inc., Rahway, N.J.

[21] Appl. No.: 899,283

[22] Filed: Aug. 22, 1986

[51] Int. Cl.⁴ .............................................. C07C 99/08
[52] U.S. Cl. .................................... 562/446; 562/401
[58] Field of Search ................................ 562/448, 401

[56] References Cited

U.S. PATENT DOCUMENTS

| | | | |
|---|---|---|---|
| 2,605,282 | 7/1952 | Britton et al. | 562/446 |
| 3,405,159 | 10/1968 | Krieger et al. | 562/401 |
| 3,676,482 | 7/1972 | Hinkley et al. | 562/446 |
| 3,721,697 | 3/1973 | Reinhold et al. | 562/446 |
| 3,892,539 | 7/1975 | Midler | 23/301 R |
| 4,005,127 | 1/1977 | Knowles et al. | 562/446 |
| 4,380,646 | 4/1983 | Franzmann | 562/446 |
| 4,436,910 | 3/1984 | Kleemann et al. | 562/446 |

OTHER PUBLICATIONS

Kaigorodova et al, Isvestiya Okal Nauk SSSR, vol. 5, pp. 1001–1004 (1984).
Secor, Chem. Review, 80, pp. 297–308.

Primary Examiner—James H. Reamer
Attorney, Agent, or Firm—Alice O. Robertson; Michael C. Sudol

[57] ABSTRACT

A process for the preparation of (S)- or L-3-(3,4-dihydroxyphenyl)alanine (L-dopa) is described. The process utilizes water as reaction process solvent and proceeds via formation of an intermediate which can be kinetically resolved in a polar solvent to a precursor of the desired isomer and in which the undesired isomer can be efficiently racemized for reuse.

3 Claims, No Drawings

PROCESS FOR L-DOPA

The present invention is directed to an improved process for the preparation of L-dopa.

BACKGROUND OF THE INVENTION (S) or L-3-(3,4-Dihydroxyphenyl)alanine, more commonly known as L-dopa or levodopa and represented by the formula

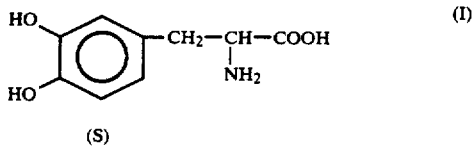

is a drug useful in the treatment of Parkinson's disease, Merck Index, Tenth Edition, pp. 784–5. The substance may be produced from natural materials such as Vicia Faba beans, U.S. Pat. No. 3,253,023, by fermentation of L-tyrosine, J. Am. Chem. Soc. 91, 6204 (1969) and by various synthetic methods. Synthetic methods include chemical asymmetric synthesis, enzymatic asymmetric synthesis and resolution methods.

In U.S. Pat. No. 4,005,127 is described a chemical asymmetric synthesis which includes the step in which the racemic mixture of a precursor compound, α-acetamido-4-hydroxy-3-methoxycinnamic acid acetate is hydrogenated in the presence of a catalyst mixture of a metal coordination complex in combination with an optically active phosphine or arsine ligand to produce the L-enantiomer of N-acetyl-3-(4-hydroxy-3-methoxyphenyl)-alanine acetate. Another asymmetric synthesis is that described by L. N. Kaigorodova et al, in Izvestiya Okal. Nauk SSSR, 5, 1090, an asymmetric reductive aminolysis of m-methoxy-p-acetoxy-α-acetamidocinnamic acid azlactone in the presence of S-α-phenylethylamine and palladium catalyst to produce an SS-diastereomer of m-methoxy-p-acetoxy-N-acetylphenylalanine-α-phenylethylamide which after crystallization and hydrolysis produced pure L-dopa.

Resolution methods include the traditional method of treating a racemic mixture with an optically active material to form derivatives and thereafter physically separating the derivatives, and the kinetic crystallization technique where one isomer of the racemic mixture preferentially crystallizes. A number of the latter type which have been carried out in the laboratory are listed in Chemical Reviews, 80, 228 (1980).

Many of the reported literature methods are not adaptable as a synthetic method suitable for preparing commercial quantities of L-dopa because of slowness of reaction, difficulty of the separation step or difficulty in recycling the unwanted isomer. Moreover, some of the reported require hazardous or potentially hazardous materials and/or large volumes of organic solvents.

SUMMARY OF THE INVENTION

According to the present invention there has been discovered a process for producing L-dopa which utilizes the step of kinetic crystallization of (R,S)-N-acetyl-3-(4-acetoxy-3-methoxyphenyl)alanine which gives excellent overall yields, is adaptable for large scale operation, avoids the use of hazardous organic solvents in the process steps, provides for efficient recyclization of the undesired isomer, and further utilizes commercially available starting materials.

The designation (R) or (S) are generally employed in this application, although the compounds of the process of the present invention are well-known and the enantiomorphic forms in the older literature are designated D and L respectively.

DESCRIPTION OF THE INVENTION

The process of the present invention for facilely producing (S)-3-(3,4-dihydroxyphenyl)alanine (L-dopa) comprises the following sequence of reactions:

(1) hydrolyzing vanillylhydantoin (II) with alkali to obtain 3-(4-hydroxy-3-methoxyphenyl)alanine (III);
(2) acetylating 3-(4-hydroxy-3-methoxyphenyl)alanine to obtain (R,S)-N-acetyl-3-(4-acetoxy-3-methoxyphenyl)alanine (IV);
(3) selectively and independently crystallizing the enantiomorphs, (S)-N-acetyl-3-(4-acetoxy-3-methoxyphenyl)alanine (Va), and (R)-N-acetyl-3-(4-acetoxy-3-methoxyphenyl)alanine (Vb) in a simultaneous or a sequential operation
(4) hydrolyzing the (S)-N-acetyl-3-(4-acetoxy-3-methoxy-phenyl)alanine (Va) to obtain (S)-3-(3,4-dihydroxy-phenyl)alanine (I), and
(5) racemizing the (R)-N-acetyl-3-(4-acetoxy-3-methoxyphenyl)alanine (Vb) to obtain (R,S)-N-acetyl-3-(4-acetoxy-3-methoxyphenyl)alanine (IV) through an intermediate azlactone (4-(4-acetoxy-3-methoxybenzyl)-2-methyloxazol-2-in-5-one) (VI) and recycling said (R,S)-N-acetyl-3-(4-acetoxy-3-methoxyphenyl)alanine to Step (3).

By "selectively and independently crystallizing" as above employed is meant that preferential or selective crystallization of one enantiomorph is made to occur from a racemic mixture containing the two enantiomorphs and that the crystallization of each enantiomorph is carried out from an independent mixture. Thus, selective crystallization for different enantiomorphs may be carried out simultaneously.

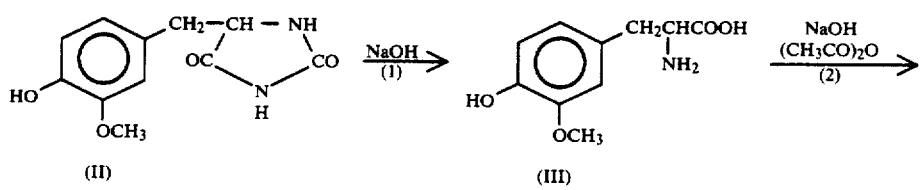

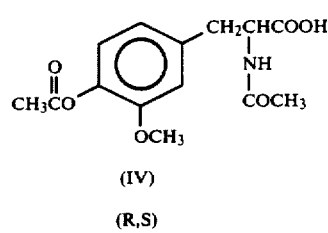
(IV)
(R,S)

-continued

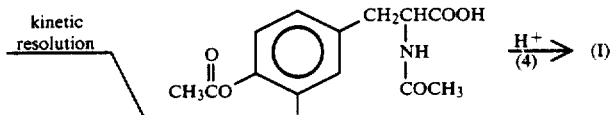

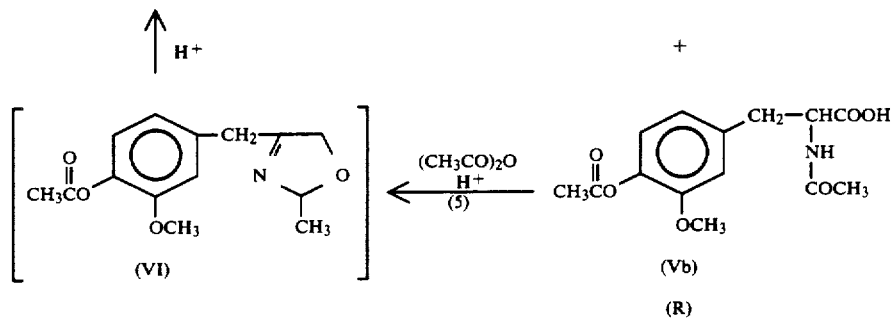

Although the foregoing process appears to entail extra steps in first hydrolyzing the vanillyl hydantoin and then acetylating, the process is highly advantageous and ultimately efficient in that the reaction steps can be carried out in water using readily available starting materials and without isolating intermediates until the racemic N-acetyl-3-(4-acetoxy-3-methoxyphenyl)alanine (IV) suitable for kinetic resolution by preferential crystallization is obtained. Moreover, the process by utilizing this intermediate provides a means for the ready racemization of the undesired isomer to produce a compound chemically identical to the compound used in the kinetic crystallization step and thus ready for immediate recycle. In addition, each step is uncomplicated, substantially free from side reactions, and produces high yields. Thus, there is provided a simple, efficient process with reliable results and advantageous from economic and safety standpoints.

The N-acetyl-3-(4-acetoxy-3-methoxyphenyl)alanine intermediate is critical and essential to the success of this process. If the amino nitrogen and the 4-hydroxy group are protected by some other acyl group, or if protected by mixed groups, or if the hydroxy group is left unprotected, the intermediate cannot be kinetically resolved.

Vanillylhydantoin, the starting material in the above procedure, may be prepared by:

(a) condensing vanillin and hydantoin by heating together in admixture with diethanolamine to produce 5-vanillylidenehydantoin, and (b) catalytically reducing the 5-vanillylidenehydantoin by contacting the same with hydrogen in the presence of palladium on carbon catalyst.

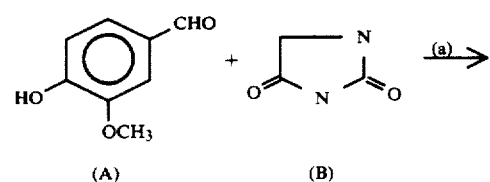

-continued

The procedure is similar to the first two steps in the Britton et al. patent, U.S. Pat. No. 2,605,282 for producing racemic L-dopa. In the present process, the product of the hydrogenation is not isolated but used directly in the process of the present invention.

In the process of the present invention, the first step of hydrolyzing vanillylhydantoin is effected by heating together 5-vanillylhydantoin with aqueous alkali to hydrolyze said vanillylhydantoin and to obtain 3-(4-hydroxy-3-methoxyphenyl)alanine. For the hydrolysis, molar excess of alkali is employed. Generally, from about 1.1 to 5 molar excess is found to be satisfactory. It is critical and essential that the hydrolysis be carried out under alkaline conditions so that the correct product for the next step is obtained directly. The hydrolysis is carried out with heating, generally in the temperature range of from about 100° to about 160° C. at pressures of from about 15 to 100 psi for from about 2 to 30, preferably 2 to 10 hours. The 3-(4-hydroxy-3-methoxyphenyl)alanine produced by this process is employed in the next step without isolation.

The second step of acetylation comprises simultaneously adding to an alkaline solution of 3-(4-hydroxy-3-methoxyphenyl)alanine, cooled to a temperature in the range 0° to 5° C., acetic anhydride and aqueous alkali at a rate such that the pH is maintained between about 10.5 and 11.5 and the temperature of the reaction mixture is maintained below about 10° C., thereafter adding acetic anhydride to the mixture until a pH of about 8.0-9.0 is reached to obtain N-acetyl-3-(4-acetoxy-3-methoxyphenyl)alanine (diacetyl compound) in the reaction mixture. The product is recovered by acidifying the mixture to a pH in the range of about 1.5 to 3 and temperature in the range 20° to 25° C., preferably in the presence of seed crystals of previously prepared N-acetyl-3-(4-acetoxy-3-methoxyphenyl)-alanine, and aging.

In this acetylation reaction, known as the Schotten-Bauman reaction, the acetic anhydride is used in slight excess on a molar basis. At least 2.1 moles, generally from about 2.1 to 6 moles of acetic anhydride are employed for each mole of 4-hydroxy-3-methoxyphenylalanine employed. The base is also employed in molar excess. However, it is essential for success of the acetylation that the amount of the base should not be so great as to raise the pH above about 12. Below this pH and temperature, the 4-acetoxy group has been found to be moderately stable. The first part of the acetylation is very exothermic and the addition of acetic anhydride and sodium hydroxide is carried out slowly in order to maintain both pH and temperature under control. Thereafter, the excess acetic anhydride is added to lower the pH to about 8.0 to 9.0 at which pH the compound is much more stable. On completion of the reaction, conveniently determined by liquid chromatographic analysis, the acetylation mixture is acidified to a pH in the range 1.5 to 3, preferably with 50 percent sulfuric acid or concentrated hydrochloric acid while the temperature is maintained between 20° and 25° C. and the pH in the range 1.5 to 3. The mixture then is allowed to stand from 1 to several hours to complete the precipitation of the crystalline racemic N-acetyl-3-(4-acetoxy-3-methoxyphenyl)alanine. An efficient method of carrying out this crystallization has been found to be to charge a vessel with water and seeds of the DL or (R,S)-N-acetyl-4-acetoxy-3-methoxyphenylalanine and simultaneously adding thereto the acetylation mixture and acid and thereafter allowing the mixture to stand to complete the crystallization. It is critical and essential that the temperature of the crystallizing mixture not be allowed to fall below 20° C. since at the lower temperatures sodium bisulfate and/or sodium sulfate crystallizes. After completion of the addition of the acetylation mixture and sulfuric acid, the slurry is aged and thereafter washed to remove sulfate and then dried. Thereafter, the crystals are recovered by filtration and washed with water and employed in the kinetic resolution step.

The third step which comprises resolving (R,S)-N-acetyl-3-(4-acetoxy-3-methoxyphenyl)alanine is effected by preparing a supersaturated solution of the racemic alanine compound in a polar solvent by warming in the solvent, then allowing the mixture to cool and contacting the solution with previously prepared seeds of (S)-N-acetyl-3-(4-acetoxy-3-methoxy-phenyl)alanine and allowing crystals of the (S)-N-acetyl-3-(4-acetoxy-3-methoxyphenyl)alanine to form in good yields. The latter then may be recovered by filtration. The (R) isomer may be recovered in a similar manner or from the mother liquid hereinafter described.

Solvents which may be employed for this resolution include water and several classes of organic solvents. One suitable class of organic solvent is lower alkyl ketones. Acetone is the preferred solvent. Methyl ethyl ketone may be employed. Secondary alcohols, preferably isopropanol may be employed. Combinations of alcohol and water, such as, methanol-water, also may be employed. Higher branched alcohols and ketones are undesirable in view of the tendency for the solution to be viscous.

Although the resolution may be carried out in a batch operation, it is contemplated and preferred that this step be operated in a continuous manner.

The equipment which may be used for continuous kinetic crystallization resolution of racemic N-acetyl-(4-acetoxy-3-methoxyphenyl)alanine is a fluidized bed crystallizer such as one described in detail in U.S. Pat. Nos. 3,892,539 and 3,510,266. Basically, the equipment consists of a dissolver with internal filters and two crystallization columns and means to pump, sonify and maintain a temperature difference between the dissolver and the crystallization columns which are for the (R) or D isomer and for the (S) or L isomer. In each column, a bed of crystals of an enantiomorph is fluidized by the upward flow therethrough of a fluidizing liquid which is a supersaturated solution of the racemic mixture so that some of the particular enantiomorph crystallizes onto the fluidized crystals which then increase in size and weight and which when sufficiently heavy migrate downward against the upward flow of the fluidizing liquid and may be recovered in substantially optically pure form. The columns may be operated in parallel or in series. When the columns are operated in parallel, the effluents from both columns are returned to the dissolver. When they are operated in series, the effluent from one column is conducted to the second column and thereafter returned to the dissolver. When the columns are operated in parallel, filters may be placed between the return flow from the columns to the dissolver to recover optically pure fines which are carried out of the columns. When the columns are operated in series, the D or (R) column preferably precedes the L or (S) column and the effluent from the (R) column is reheated to dissolve the fines. The solution then is filtered and cooled by passing through a heat exchanger before conducting it to the (S) column.

In carrying out the resolution in a continuous manner, the system is first filled at about 40° C. with a solution, preferably in acetone, of (R,S) or DL-N-acetyl-3-(4-acetoxy-3-methoxyphenyl)alanine. The dissolver is cooled to 35° C. and the two crystallization columns to 25° C. Optically pure seeds of the L and D enantiomorphs are added to the two columns. Additional racemate is added to the dissolver as needed to maintain a solid phase.

In carrying out the operation, pumping is initiated and the rate adjusted so that the seed beds are fluidized and the solids weight per liter of fluidized bed is about 50 grams per liter. Under these conditions the residence time in each column is about 5 minutes. The seed bed density is allowed to grow to 150 to 250 grams per liter of fluidized bed at which point a portion of the bed is drained to a filter and washed with cold acetone to recover the enatiomorphs which are substantially optically pure. The filtrate and washes then are returned to the dissolver.

The L or (S) enantiomorph may then be hydrolyzed in accordance with Step 4.

The D or (R) enantiomorph may then be racemized in accordance with Step 5.

The fourth step comprises hydrolyzing by intimately contacting and heating (S)-N-acetyl-3-(4-acetoxy-3-methoxyphenyl)alanine thus obtained with dilute acid, and thereafter allowing the mixture to cool to obtain the desired (S)-3-(3,4-dihydroxyphenyl)alanine product as a salt of the acid. The reaction may be carried out in water. Hydrohalic acid, especially hydrochloric acid is preferred. The preferred concentration is from about 6 to 12 N. The temperature for the hydrolysis is in the range of from about 100°–150° C., preferably about 115° C., the preferred temperature depending on the strength of acid employed and the time from about 3 to 10 hours. The mixture is concentrated to remove the excess acid and to recover the salt. The salt is then dissolved in water saturated with sulfur dioxide. Ammonia is then added to the solution to a pH in the range 4 to 5, preferably 4–4.5, the solution then cooled to 5° C. and aged.

The fifth step comprises racemizing by contacting the (R)-N-acetyl-3-(4-acetoxy-3 methoxyphenyl)alanine from the mother liquor or from the D-column with sodium acetate and acetic anhydride whereupon an azlactone (VI) is formed which spontaneously enolizes effecting racemization and producing (R,S)-N-acetyl-3-(4-acetoxy-3-methoxyphenyl)alanine. The latter may be recycled to Step 3 or to the dissolution vessel in a continuous crystallizer as subsequently described.

The racemization is preferably carried out in acetic acid. Preferably one equivalent each of sodium acetate and acetic anhydride are employed. If the amount of acetic anhydride is decreased to 0.5 equivalent, the racemization time is increased by a factor of about 1.7. In the absence of sodium acetate, racemization still occurs but the rate of racemization is half the rate. When sodium acetate is not employed, more acetic acid is necessary to achieve complete solubilizing of the D or (R)-N-acetyl- 3-(4-acetoxy-3-methoxyphenyl)alanine. The reaction is preferably carried out with warming in the range 45° to 55° C., preferably about 50° C. Below 45° C., the reaction time is increased to about double or greater.

In carrying out the racemization process, acetic anhydride, sodium acetate and (R)-N-acetyl-3-(4-acetoxy-3-methoxyphenyl)alanine are stirred together in acetic acid, and heated to a homogeneous solution with the formation of the azlactone. After completion of the heating, the reaction mixture containing the azlactone is quenched by adding water and the mixture then heated to distill off the acetic acid to minimize product loss attributable to solubility of the diacetyl compound product in acetic acid. The acetylation mother liquor from Step 2, or acidified water or acidified sodium sulfate solution is then added to the solution to complete the precipitation of (R,S)-N-acetyl-3-(4-acetoxy-3-methoxyphenyl)alanine.

The (R,S)-N-acetyl-3-(4-acetoxy-3-methoxyphenyl)alanine thus obtained may be recovered by conventional procedures and recycled to Step 3.

The preferred embodiment of the present invention comprises:

(1) heating an aqueous solution of 5-vanillylhydantoin in excess alkali in an autoclave (about 15 to 100 psi) at a temperature in the range of 100° to 160° C. for from 2 to 10 hours, thereafter cooling to a temperature below about 100° C. and distilling until the ammonia by-product is removed to obtain an alkaline solution of 3-(3-methoxy-4-hydroxyphenyl)alanine;

(2) cooling the alkaline solution to a temperature in the range of about 0° to 10° C., and simultaneously adding acetic anhydride and sodium hydroxide solution at a rate such that the temperature of the reaction mixture is maintained below about 5° C. and the pH maintained between 10.5 and 11.5, thereafter carefully adding additional acetic anhydride to a pH in the range of about 8 to 9 to obtain racemic N-acetyl-3-(4-acetoxy-3-methoxyphenyl)alanine in the reaction mixture, and then crystallizing said acetylated alanine compound by acidifying the acetylation mixture with 50 percent sulfuric acid or concentrated hydrochloric acid to a pH of about 1.5 to 3.0, preferably, 1.7–2.0 at temperatures maintained in the range of 20°–25° C. in the presence of previously prepared (R,S)-N-acetyl-3-(4-acetoxy-3-methoxyphenyl)alanine crystals;

(3) intimately mixing and dissolving with warming to 34°–41° C. racemic N-acetyl-3-(4-acetoxy-3-methoxyphenyl)alanine in a polar solvent to form a supersaturated solution thereof, loading said solution onto a fluid crystallizer comprising a dissolver and two crystallization columns, for the enantiomorphs, then cooling the dissolver to 34°–36° and the crystallization column to 24°–26° C., adding optically pure seeds of the L or (S) and D or (R) enantiomorphs to the columns, then fluidizing the beds to cause crystal formation of the desired enantiomorphs in the respective columns, and separately recovering the (S)-N-acetyl-3-(4-acetoxy-3-methoxyphenyl)alanine and (R)-N-acetyl-3-(4-acetoxy-3-methoxyphenyl)alanine.

(4) intimately contacting (S)-N-acetyl-3-(4-acetoxy-3-methoxyphenyl)alanine with acid, heating the resulting mixture to hydrolyze the acetylated alanine compound, distilling to remove excess acid and then cooling to obtain the (S)-3-(3,4-dihydroxyphenyl)alanine product as a salt; thereafter dissolving the salt in water, adding base to bring the pH to 4 to 4.5 then cooling to 0°–5° C. and aging for 1 to 5 hours to obtain as crystalline solid, the desired (S)-3-(3,4-dihydroxyphenyl)alanine; and (5) intimately contacting and heating together in acetic acid, (R)-N-acetyl-3-(4-acetoxy-3-methoxyphenyl)alanine or solid rich in said isomer (obtained by concentrating the mother liquor from Step 3) or (R)-N-acetyl-3-(4-acetoxy-3-methoxyphenyl) alanine obtained from the D-crystallization column with sodium acetate and acetic anhydride to form an azlactone of said alanine compound in the reaction mixture, quenching the reaction mixture with water, distilling off some of the acetic acid, then adding thereto the mother liquor from the acetylation process to precipitate (R,S)-N-acetyl-3-(4-acetoxy-3-methoxyphenyl)alanine in the reaction mixture, thereafter recovering the racemic diacetyl compound and recycling to Step (3).

The vanillylhydantoin starting material used in the present process may be prepared from readily available materials, vanillin and hydantoin, employing a method similar to the first two steps of the method of the afore-cited Britton et al. patent for the synthesis of DL dopa. Thus, it may be prepared by (1) condensing vanillin and hydantoin to obtain 5-vanillylidenehydantoin, and thereafter (2) catalytically hydrogenating 5-vanillylidenehydantoin to obtain vanillylhydantoin.

The preparation of 5-vanillylidenehydantoin may be carried out using the procedure described in the Britton et al. patent which is incorporated herein by reference.

The 5-vanillylhydantoin may be prepared in a manner similar to that described in the Britton patent but with the modification that the hydrogenation mixture containing the product is employed directly in the hydrolysis step without isolation. The 5-vanillylidenehydantoin is hydrogenated in the presence of palladium on carbon (Pd-C) catalyst in aqueous alkali. The hydrogenation is carried out at a temperature of from about 40° to 50° C. under a pressure of about 40 pounds per square inch gauge (psig) until completion of the reaction as indicated by cessation in the uptake of hydrogen. The reduction solution is filtered while warm (55°–60° C.) to remove the catalyst and the filtrate containing 5-vanillylhydantoin is employed directly in the hydrolysis step.

The following example illustrates the invention but is not to be construed as limiting.

Preparation of 5-vanillylhydantoin 234 grams (1.0 mole) of 5-vanillylidenehydantoin previously prepared in a manner similar to that described in the Britton patent was slurried in 1.11 liters of 1N sodium hydroxide (1.11 mole) and together with 11.7 grams of 5% Pd-C catalyst was charged to a Parr pressure flask and shaken at 40 pounds per square inch gauge pressure and 50° C. until hydrogen uptake ceased (2.75 hours) to obtain therein, a reduction product comprising the 5-vanillylhydantoin. The reduction solution was warmed to 55°–60° C. and filtered through filtering aid to remove the catalyst. The catalyst was washed with three 25 milliliter portions of hot water. The filtrate containing 5-vanillylhydantoin was employed in the next step.

Preparation of 3-(4-hydroxy-3-methoxyohenyl)alanine

To 1350 milliliters of 5-vanillylhydantoin solution above prepared, was added with stirring 311 grams (204 ml, 3.89 moles NaOH) of 50 percent aqueous sodium hydroxide solution. The warm solution was placed in a rocking autoclave and heated to 150° C. and then at 150° C. for one hour to effect hydrolysis with the formation of 3-(4-hydroxy-3-methoxyphenyl)alanine in the alkaline medium. The reaction mixture was then cooled, vented to remove ammonia and transferred to a vessel and concentrated under reduced pressure (23 inches Hg) at 80° C. The concentrated alkaline mixture containing 3-(4-hydroxy-3-methoxyphenyl)alanine was employed directly in the acetylation reaction.

Preparation of (R,S)-N-acetyl-3-(4-acetoxy-3-methoxyphenyl)alanine

A. Acetylation

A 540 milliliter aliquot (containing 0.51 mole of 3-(4-hydroxy-3-methoxyphenyl)alanine) was charged to a vessel equipped with a mechanical stirrer, two addition funnels, pH electrode, nitrogen inlet and thermometer, and the mixture cooled to 0°–5° C. 146 milliliters (153 grams, 1.5 moles) of acetic anhydride and 130 milliliters (0.65 mole) of 5N sodium hydroxide solution were added simultaneously to the amino acid solution at a rate to maintain the pH between 10.5-11.5 and the temperature below 10° C. After completion of the addition of sodium hydroxide, the remaining acetic anhydride was added until the pH of the solution was within the range 8.0 to 9.0 to complete the formation of (R,S)-N-acetyl-3-(4-acetoxy-3-methoxyphenyl) alanine in the reaction mixture. Completeness of the reaction was determined by liquid chromatographic analysis employing 82:18:01/water:acetonitrile: phosphoric acid.

B. Crystallization

A vessel, equipped as for the foregoing acetylation, was charged with 280 milliliters of water and 0.1 gram of DL-seeds. The acetylation mixture amounting to 820 milliliters and 50 percent sulfuric acid amounting to 260 milliliters were added simultaneously to the aqueous medium while the pH was maintained at 1.7 ±2 and the temperature was maintained between 20° C. and 25° C. After addition of 100 milliliters of the acetylation mixture, the reaction became cloudy and the addition was interrupted for about 10 minutes to permit a seed bed to develop. After completion of the addition, the slurry was aged for about 30 minutes, then filtered to obtain a precipitate of racemic N-acetyl-3-(4-acetoxy-3-methoxyphenyl)alanine which then was washed with eight 75 milliliter portions of 20°–25° C. water to a negative test for sulfate with barium hydroxide solution. The precipitate after drying in vacuo at 50° C. amounted to 131.3 grams or 87.2 percent yield. The N-acetyl-3-(4-acetoxy-3-methoxyphenyl)alanine intermediate had the following analyses: KF =0.01%; NaOH titration =100.7%; UV =$\lambda_{max}$ =79 (pH 7 buffer) and m.p =156°–158.5° C.

The mother liquor is retained for use in racemization of the D or (R) isomer.

Preparation of (S)-N-acetyl-3-(4-acetoxy-3-methoxyphenyl)alanine

The apparatus employed is a system comprising a dissolver and two crystallization columns and equipped with a pump, sonifier and means for temperature control is employed. The system is filled with a 40° C. acetone solution of (R,S)-N-acetyl-3-(4-acetoxy-3-methoxyphenyl)alanine at a concentration of 45 mg/ml. The dissolver is then cooled to 35° C. and the two crystallization columns to 25° C. Optically pure seeds of the (S) and (R) enantiomorphs are added to the two columns. Racemate is added to the dissolver as needed to maintain the solid phase. The pumping is started. The pumping rate is adjusted so that the seed beds are fluidized and the solids weight per liter of the fluidized bed adjusted to about 50 grams per liter. The seed bed density is allowed to grow to 150-250 grams per liter of fluidized bed, at which point, a portion of the bed is drained to a filter and washed with cold acetone. The filtrate and washes are returned to the dissolver. The (S) and (R) enantiomorphs are substantially optically pure, m.p. 172°–175° C. ($[\alpha]_{405}^{25}$ =133°, C=1 in 90% ethanol)

Preparation of (S) or L-3-4-dihydroxyohenylalanine 29.5 grams of optically pure (S) or L-N-acetyl-3-(4-acetoxy-3-methoxyphenyl)alanine and 100 milliliters of 12N hydrochloric acid are placed in a pressure tube, the tube is cooled in a dry ice-acetone bath, flushed with nitrogen and sealed. The sealed tube is heated at 115°–120° C. for about 4 hours in a rocking autoclave. At the end of this period, the tube is cooled in a dry ice-acetone bath, then opened and the contents concentrated under reduced pressure to a thick slurry. The slurry is flushed with two 50 milliliter portions of water. The residue is dissolved in 100 milliliters of water and to the resulting solution is added in order: 20 milligrams of ethylenediaminetetraacetic acid disodium salt, 0.154 gram of sulfur dioxide and 1.0 gram of activated charcoal. The resulting mixture is stirred under a blanket of nitrogen for about 15 minutes, filtered through Supercel filter aid and the cake washed with distilled water. The filtrate then is heated to 60° C. under a blanket of nitrogen and the pH adjusted to 4.5-5.0 with concentrated ammonia, cooled to 10° C. and aged for 1.5 hours to obtain the desired (S) or L-3,4-dihydroxyphenylalanine. The product is filtered, washed free of chloride with cold (0°–5° C.) water and dried at 45° C. under reduced pressure (about 10 mm-Hg). The product obtained in good yields is an optically pure white solid. The melting point of (S)-or L-3,4-dihydroxyphenylalanine is 276°–278° C.

Racemization of (R) or D-N-acetyl-3-(4-acetoxy-3-methoxyphenyl)alanine 5.06 grams of (R)-N-acetyl-3-(4-acetoxy-3-methoxyphenyl)alanine and 1.41 grams of sodium acetate were suspended in 20 milliliters of glacial acetic acid under nitrogen and the mixture was heated to 50° C. 1.65 milliliters of acetic anhydride were added to the mixture in one portion and the resulting solution heated at 50° C. with stirring for about 2.5 hours. Then, the reaction mixture was cooled in an ice bath, 10 milliliters of water was added thereto, and the resulting mixture concentrated to a light yellow oil. Thereafter, 25 milliliters of acetylation mother liquors were added to the concentrate, resulting in a solution with a pH of 3.6. The pH was adjusted to 2.5 by adding dropwise 1 milliliter of 50 percent sulfuric acid solution whereupon a white solid of racemic N-acetyl-3-(4-acetoxy-3-methoxyphenyl)alanine precipitated in the reaction mixture. The resulting slurry was aged at 20°-25° C. for about one-half hour and the solid recovered by filtration and washed several times with water until the wash indicated absence of sulfate. The product then was dried at 60° C. at reduced pressured to obtain 4.62 grams (90.2 percent yield) of racemic N-acetyl-3-(4-acetoxy-3-methoxyphenyl)alanine; m.p. 155°-158° C.; $[\alpha]_D^{25} = -0.6$; LC weight percent 97.8%.

What is claimed is:

1. A process for producing (S)-3-(3,4-dihydroxyphenyl)alanine which comprises:
(1) hydrolyzing 5-vanillylhydantoin with alkali to obtain 3-(4-hydroxy-3-methoxyphenyl)alanine;
(2) acetylating 3-(4-hydroxy-3-methoxyphenyl)alanine in aqueous alkali to obtain (R,S)-N-acetyl-3-(4-acetoxy-3-methoxy- phenyl)alanine;
(3) selectively and independently crystallizing the enantiomorphs, (S)-N-acetyl-3-(4- acetoxy-3-methoxyphenyl)alanine and (R)-N-acetyl-3-(4-acetoxy-3-methoxyphenyl)alanine in a parallel or a series operation;
(4) hydrolyzing (S)-N-acetyl-3-(4-acetoxy-3-methoxyphenyl)alanine to obtain (S)-3-(3,4-dihydroxyphenyl)alanine; and
(5) racemizing (R)-N-acetyl-3-(4-acetoxy-3-methoxyphenyl)alanine by warming an acetic acid dispersion thereof with acetic anhydride to obtain (R,S)-N-acetyl-3-(4-acetoxy-3-methoxyphenyl)-alanine; and recycling the (R,S)-N-acetyl-3-(4-acetoxy-3-methoxyphenyl)alanine to Step 3.

2. A process for producing (S)-3-(3,4-dihydroxyphenyl)alanine which comprises:
(1) heating an aqueous basic solution of 5-vanillylhydantoin in excess alkali at a temperature in the range of 100° to 160° C. and pressure of 15 to 100 psi for from 2 to 10 hours, thereafter cooling to a temperature below about 100° C. and venting the ammonia by-product to obtain an alkaline solution of 3-(3-methoxy-4-hydroxyphenyl)alanine;
(2) cooling the alkaline solution to a temperature in the range of about 0° to 5° C., simultaneously adding acetic anhydride and sodium hydroxide solution at a rate such that the temperature of the reaction mixture is maintained below about 10° C. and the pH maintained between about 10.5 and 11.5, thereafter carefully adding additional acetic anhydride to a pH in the range of about 8.0 to 9.0 to obtain racemic N-acetyl-3-(4-acetoxy -3-methoxyphenyl)alanine in the reaction mixture and crystallizing said acetylated alanine compound by acidifying the acetylation mixture to a PH in the range of about 1.5-3.0 while the temperature is maintained in the range of 20°-25° C., preferably in the presence of crystals of previously prepared seed crystals of (R,S)-N-acetyl-3-(4-acetoxy-3-methoxyphenyl)alanine to obtain the alanine compound as a crystalline solid;
(3) intimately mixing and dissolving with warming to 39°-41° C., racemic N-acetyl-3-(3-acetoxy-3-methoxyphenyl)alanine in a polar solvent to form a supersaturated solution thereof, loading said solution onto a fluid crystallizer comprising a dissolver and two crystallization columns for the enantiomorphs, thereafter cooling the dissolver to 34°-36° C. and the crystallization column to 24°-26° C., adding optically pure seeds of L or (S) and D or (R) enantiomorphs to the columns then fluidizing the beds to cause crystal formation of the desired enantiomorphs in the respective columns, and separately recovering the (S)-N-acetyl- 3-(4-acetoxy-3-methoxyphenyl)alanine and (R)-N-acetyl-3-(4-acetoxy-3-methoxyphenyl)alanine.
(4) intimately contacting (S)-N-acetyl-3-(4-acetoxy-3-methoxyphenyl)alanine with acid, heating the resulting mixture to hydrolyze the acetylated alanine compound, distilling to remove excess acid and then cooling to obtain (S)-3-(3,4-dihydroxyphenyl)alanine as a salt, thereafter dissolving the salt in water and adjusting the pH to 5.2 with base and then cooling to 0°-5° C. and aging to obtain the desired (S)-3-(3,4-dihydroxyphenyl)-alanine product as a crystalline solid; and
(5) intimately contacting and heating together in acetic acid, (R)-N-acetyl-3-(4-acetoxy3-methoxyphenyl)alanine or solid rich in said enantiomorphs or (R)-N-acetyl-3-(4-acetoxy-3-methoxyphenyl)alanine obtained from the D-crystallization column obtained from Step 3, with sodium acetate and acetic anhydride to form the azlactone of said alanine compound in the reaction mixture, quenching the reaction mixture with water, distilling off some of the acetic acid, then adding thereto the mother liquor from the acetylation process to precipitate (R,S)-N-acetyl-3-(4-acetoxy-3-methoxyphenyl)alanine in the reaction mixture, thereafter recovering the racemic diacetyl compound and recycling to Step (3).

3. A process according to claim 2 wherein in Step (2) equivalent amounts of 3-(3-methoxy-4-hydroxyphenyl)alanine, acetic anhydride and sodium acetate are employed; and wherein the acetylation mixture is adjusted to pH of about 1.7 and added to an aqueous solution containing crystals of (R,S)-N-acetyl-3-(4-acetoxy-3-methoxyphenyl)alanine.

* * * * *

UNITED STATES PATENT AND TRADEMARK OFFICE
CERTIFICATE OF CORRECTION

PATENT NO. : 4,716,246

DATED : December 29, 1987

INVENTOR(S) : Donald F. Reinhold, et al.

It is certified that error appears in the above-identified patent and that said Letters Patent is hereby corrected as shown below:

Claim 2, column 12, line 7, "PH" should be --pH--

Claim 2, column 12, line 38, "acetoxy 3" should be

-- acetoxy-3 --

Signed and Sealed this

Fifth Day of July, 1988

*Attest:*

DONALD J. QUIGG

*Attesting Officer*    *Commissioner of Patents and Trademarks*